United States Patent [19]
Lowther et al.

[11] Patent Number: 5,609,868
[45] Date of Patent: Mar. 11, 1997

[54] PHARMACEUTICAL COMPOSITIONS COMPRISING HYBRID α-INTERFERON

[75] Inventors: Nicholas Lowther, Southwater; John D. Allen, Worthing; Colin Howes, Horsham, all of England

[73] Assignee: Ciba-Geigy Corporation, Tarrytown, N.Y.

[21] Appl. No.: 288,671

[22] Filed: Aug. 10, 1994

[30] Foreign Application Priority Data

Aug. 13, 1993 [GB] United Kingdom .................. 9316849
Mar. 24, 1994 [GB] United Kingdom .................. 9405879

[51] Int. Cl.⁶ .......................... A61K 38/21; C07K 14/52
[52] U.S. Cl. ...................... 424/857; 424/85.4; 530/351
[58] Field of Search ................................ 424/85.7, 85.1, 424/85.4; 530/351

[56] References Cited

U.S. PATENT DOCUMENTS 4,847,079  7/1989  Kwan ..................... 424/85.7

FOREIGN PATENT DOCUMENTS 0205404   12/1986  European Pat. Off. .
0331635    9/1989  European Pat. Off. .
59-196823 11/1984  Japan .
8904177    5/1989  WIPO .

OTHER PUBLICATIONS

Morehead et al. "Roles of the 29–138 Disulfide Bond of Subtype A of Human Interferon in its Antiviral Activity and Conformational Stability" Biochemistry 1984, vol. 23. (2500–2507) 1984.
H.K. Hochkeppel et al "Human Ien–Alpha Hybrids" Drugs of the Future vol. 17, No. 10 (1992.) pp. 899–914.
59196823 – Abstract of Japan.

Primary Examiner—Ponnathapura Achutamurthy
Attorney, Agent, or Firm—Henry P. Nowak; Irving M. Fishman

[57] ABSTRACT

The present invention provides a stable aqueous solution of hybrid α-Interferon which contains as the stabilizer a buffer at a pH of from 3.0 to 5.0.

32 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 166 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( i x ) FEATURE:
        ( A ) NAME/KEY: Disulfide-bond
        ( B ) LOCATION: order(1..99, 29..139)

( x i ) SEQUENCE DESCRIPTION: SEQ ID NO:1:

```
Cys Asp Leu Pro Gln Thr His Ser Leu Gly Asn Arg Arg Ala Leu Ile
 1               5                  10                  15

Leu Leu Ala Gln Met Arg Arg Ile Ser Pro Phe Ser Cys Leu Lys Asp
                20                  25                  30

Arg His Asp Phe Glu Phe Pro Gln Glu Glu Phe Asp Asp Lys Gln Phe
                35                  40                  45

Gln Lys Ala Gln Ala Ile Ser Val Leu His Glu Met Ile Gln Gln Ile
            50                  55                  60

Phe Asn Leu Phe Thr Thr Lys Asp Ser Ser Ala Ala Trp Asp Glu Asp
 65                 70                  75                  80

Leu Leu Asp Lys Phe Cys Thr Glu Leu Tyr Gln Gln Leu Asn Asp Leu
                85                  90                  95

Glu Ser Cys Val Met Gln Glu Val Gly Val Ile Glu Ser Pro Leu Met
               100                 105                 110

Tyr Glu Asp Ser Ile Leu Ala Val Arg Lys Tyr Phe Gln Arg Ile Thr
           115                 120                 125

Leu Tyr Leu Thr Glu Lys Lys Tyr Ser Ser Cys Ala Trp Glu Val Val
       130                 135                 140

Arg Ala Glu Ile Met Arg Ser Phe Ser Leu Ser Ile Asn Leu Gln Lys
145                 150                 155                 160

Arg Leu Lys Ser Lys Glu
               165
```

PHARMACEUTICAL COMPOSITIONS COMPRISING HYBRID α-INTERFERON

The present invention relates to stable aqueous compositions containing α-Interferon hybrid.

The Interferons are families of inducible secretory proteins produced in response to viral and other stimuli. The α-Interferons are currently being used clinically for the treatment of a number of different disease states which include: Hairy-cell leukaemia, Karposi's sarcoma in AIDS, chronic Non-A, Non-B hepatitis and Basal cell carcinoma.

Recombinant human α-Interferon B/D hybrid moieties have been constructed carrying various portions of the sequence of the parent α-Interferon B and D species in order to create molecules with advantageous properties (A. Meister, G. Uz, K. E. Mogensen, J. Gen. Virol. 67, 1633, (1986)). The parent molecules are cleaved in order to exchange the DNA segments coding for peptide sequences 1–60, 61–92, 93–150 and 151–166. The BDBB hybrid has been found to exhibit particularly interesting preclinical anti-viral and anti-proliferative activity (H. K. Hochkeppel, M. Gruetter, M. A. Horisberger, J. K. Lazdins, Drugs of the Future, 17 (10), 899, (1992)). Proteins, such as α-Interferon BDBB, possess complex chemical and physical properties which cause difficulties in the purification, separation, storage and delivery of these species. Hence, the formulation of protein medicinal agents differs greatly from that of rigid small organic molecules. Several classes of excipients have been employed in parenteral formulations of proteins and peptides. Since proteins have poor oral bioavailability, the most common approach is to present them as injectable products in order to achieve efficient drug delivery. Because of the instability in solution, proteins are, generally, formulated as lyophilised (freeze-dried) powders for reconstitution immediately prior to injection by subcutaneous, intramuscular or intravenous routes.

Protein degradation can be separated into two categories, namely chemical stability and physical stability. Chemical stability refers to all processes whereby the protein is chemically modified via bond cleavage or formation. Physical stability does not involve covalent modification, but rather changes in the higher order structure of the protein, e.g. via denaturation, aggregation or precipitation. It is desirable to maintain hybrid α-Interferon BDBB in a disaggregated state in order to eliminate any possible adverse immunogenic effects and/or inconsistent dosing during therapy.

At a desirable concentration for use as an injectable therapeutic agent, hybrid α-Interferon BDBB is physically unstable in water. Its solubility is compromised and it exists in an aggregated state. Hence, stabilising excipients must be employed.

We have found that hybrid α-Interferon exists in an aggregated state when formulated in solution at neutral pH (phosphate buffered). In addition, the solubility of the protein appears to be compromised under such conditions, and very little actually dissolves.

We have now found that formulation of hybrid α-Interferon in aqueous solution at low pH stabilises the protein, and maintains it in the desirable monomeric state, and enables more to dissolve into solution.

Accordingly, the present invention provides a stable aqueous solution of hybrid α-Interferon which contains as the stablisier a buffer at a pH of from 3.0 to 5.0.

The pH of the solution is preferably from 4.0 to 4.5.

The hybrid α-Interferon is preferably α-Interferon BDBB (SEQ. ID No. 1).

The buffer salt chosen should be pharmaceutically acceptable, e.g. glycine/HCl or sodium citrate and preferably present at a concentration between 20–400 mM. The preferred buffer salt is glycine/HCl at a concentration of 50–150 mM.

A pharmaceutically acceptable polyol, e.g. mannitol, glucose or sucrose may also be employed preferably at a concentration of 20–500 mM. The preferred polyol is mannitol at a concentration of 100–250 mM. The polyol is mainly used to adjust the tonicity of the solutions to physiological values.

The hybrid α-Interferon is preferably present at a concentration of 0.1–1.5 mg/ml. The most preferred range is 0.2–0.4 mg/ml.

The hybrid α-Interferon is normally isolated and purified by a multi-stage procedure and stored as a frozen bulk solution in a buffer system of pH 7 which is not pharmaceutically acceptable. In order to produce the stable solutions of the invention it is necessary to exchange this buffer system for one which is pharmaceutically acceptable at the desired pH. This can be carried out by adding the desired buffer, subjecting the solution to ultrafiltration, adding buffer and repeating the cycle several times. Other methods may be employed such as gel filtration chromatography.

The formulations of the invention are suitable for use as pharmaceuticals for the indications mentioned above by subcutaneous, intramuscular or intravenous injection.

The invention is illustrated by the following Examples.

EXAMPLE 1

Preparation of stable 0.3 mg/ml hybrid α-Interferon BDBB citrate solution formulation at pH 4.0:—

Stock bulk solution of hybrid α-Interferon BDBB (2.6 mg/ml in 200 mM ammonium chloride/20 mM tris(hydroxymethyl)methylamine at pH 7.0) is made up to 50 ml with 40 mM sodium citrate/citric acid buffer at pH 4.0 in an ultrafiltration cell (Amicon) equipped with a 10KDa Mwt cut-off membrane (Amicon YM10). The cell is pressurised to 50–60 psi using oxygen-free nitrogen. The volume is reduced, but not to such an extent that the protein will precipitate, with continuous stirring to minimise protein concentration at the surface of the membrane, and diluted back to 50 ml with 40 mM sodium citrate/citric acid buffer at pH 4.0. This cycle is repeated 5 times. The pH of the final solution is verified as 4.0. The protein content of the final solution is verified as 0.3 mg/ml using standard procedures (Bradford assay, Bio-Rad).

The formulation, described above is sterile filtered and filled, aseptically, into 2 ml pharmaceutical grade Type 1 glass vials and sealed with teflon coated rubber septa/aluminium crimp caps. The vials are stored at 4° C., in the dark. At given time intervals, samples are analysed by reverse phase hplc (an index of chemical stability) and size exclusion chromatography (a measure of the aggregation state of the protein in solution). The reverse phase hplc results, expressed as the % hybrid α-Interferon of total peak area are presented below:—

| 4° C. Storage time/days | [hybrid α-Interferon] % total peak area |
|---|---|
| Initial | 96.53 |
| 12 | 96.05 |
| 21 | 96.64 |
| 25 | 96.43 |
| 26 | 96.30 |
| 33 | 95.00 |

| 4° C. Storage time/days | [hybrid α-Interferon] % total peak area |
| --- | --- |
| 44 | 96.33 |
| 45 | 95.37 |
| 49 | 95.34 |
| 70 | 94.62 |
| 92 | 94.83 |
| 111 | 94.08 |
| 136 | 94.00 |

The results are expressed as the means of replicate (generally 3–5) injections. The coefficient of variation (cv) for these determinations is <0.3%.

The degradation appears to follow pseudo-first order kinetics. By extension of the best-fit straight line through the data, an estimate of shelf-life, defined as the time taken to degrade to 95% (t95) of the initial content of hybrid α-Interferon BDBB, can be made. This formulation has a predicted shelf-life of at least 8 months at 4° C.

Size exclusion chromatography (SEC) reveals no detectable formation of aggregates after storage for 136 days at 4° C.

EXAMPLE 2

Example 1 is repeated except that the solution also contains 200 mM mannitol. Stability testing is carried out as in Example 1, but with storage at different temperatures, as shown below, for accelerated trials.

| Storage temperature/time | [hybrid α-Interferon] % total peak area |
| --- | --- |
| 25° Initial | 96.33 |
| 1 week | 96.07 |
| 2 weeks | 94.59 |
| 3 weeks | 94.07 |
| 4 weeks | 93.51 |
| 6 weeks | 91.83 |
| 13 weeks | 86.57 |
| 30° Initial | 96.32 |
| 3 weeks | 93.22 |
| 6 weeks | 87.72 |
| 13 weeks | 78.91 |
| 40° C. Initial | 96.34 |
| 1 week | 94.39 |
| 2 weeks | 86.04 |
| 6 weeks | 68.99 |

The degradation appears to follow pseudo-first order kinetics. Using the method described in Example 1, the formulation has a predicted shelf life of over 6 weeks at 25° C.

EXAMPLE 3

Preparation of stable 0.3 mg/ml hybrid α-Interferon BDBB glycine solution formulation at pH 4.0:—

Using an analogous procedure to that described in Example 1, stock bulk solution of hybrid α-Interferon BDBB (2.6 mg/ml in 200 mM ammonium chloride/20 mM tris(hydroxymethyl)methylamine at pH 7.0) is converted to a 0.3 mg/ml solution of the protein in 80 mM glycine/HCl buffer at pH 4.0.

Stability testing of the stable hybrid α-Interferon BDBB glycine solution formulation at pH 4.0 is carded out following the procedures described in Example 1. The results are:—

| 4° C. Storage time/days | [hybrid α-Interferon] % total peak area |
| --- | --- |
| Initial | 96.93 |
| 9 | 96.04 |
| 19 | 95.50 |
| 21 | 96.49 |
| 44 | 95.83 |
| 49 | 95.45 |
| 92 | 95.50 |
| 136 | 95.26 |

The degradation appears to follow pseudo-first order kinetics. Using the method described in Example 1, the formulation has a predicted shelf-life of at least 18 months at 4° C.

SEC reveals no significant formation of aggregated species after storage at 4° C. for 136 days.

EXAMPLE 4

Example 3 is repeated except that the solution also contains 200 mM mannitol. Stability testing is carried out as in Example 3, but with storage at different temperatures as shown below.

| Storage temperature/time | [hybrid α-Interferon] % total peak area |
| --- | --- |
| 4° C. Initial | 98.03 |
| 1 week | 97.73 |
| 4 weeks | 96.92 |
| 8 weeks | 97.73 |
| 15 weeks | 97.64 |
| 20 weeks | 97.54 |
| 30 weeks | 97.60 |
| 40° C. Initial | 98.03 |
| 1 week | 95.22 |
| 2 weeks | 92.97 |
| 4 weeks | 84.61 |

The degradation appears to follow pseudo-first order kinetics. Using the method described in Example 1, the formulation has a predicted shelf life of at least 5 years at 4° C.

SEC reveals no significant formation of aggregated species after storage at 4° C. for 20 weeks or after storage at 40° C. for 4 weeks.

EXAMPLE 5

Example 3 is repeated except that the concentration of glycine/HCl buffer is 318 mM. Stability testing is carried out as in Example 3, but with storage at different temperatures as shown below.

| Storage temperature/time | [hybrid α-Interferon] % total peak area |
| --- | --- |
| 4° C. Initial | 97.22 |
| 2 weeks | 96.34 |
| 4 weeks | 96.46 |
| 8 weeks | 95.66 |
| 40° C. Initial | 97.22 |
| 1 week | 91.16 |
| 2 weeks | 85.60 |
| 4 weeks | 77.41 |

The degradation appears to follow pseudo-first order kinetics. Using the method described in Example 1 the formulation has a predicted shelf life of at least 6 months at 4° C.

We claim:

1. A stable aqueous solution of hybrid α-Interferon which contains as the stabiliser a buffer at a pH of from 3.0 to 5.0; and wherein, the hybrid α-Interferon is α-Interferon BDBB (SEQ. ID NO. 1).

2. A stable solution as claimed in claim 1 which has a pH of from 4.0 to 4.5.

3. A stable solution as claimed in claim 1 in which the buffer is glycine/HCl or sodium citrate.

4. A stable solution as claimed in claim 1 in which the buffer is present at a concentration of 20–400 mM.

5. A stable solution as claimed in claim 1 in which the buffer is glycine/HCl at a concentration of 50–150 mM.

6. A stable solution as claimed in claim 1 in which the hybrid α-Interferon is at a concentration of 0.1 to 1.5 mg/ml.

7. A stable solution as claimed in claim 6 in which the hybrid α-Interferon is at a concentration of 0.2 to 0.4 mg/ml.

8. A stable solution as claimed in claim 1 which also contains a pharmaceutically acceptable polyol.

9. A stable solution as claimed in claim 8 in which the polyol is mannitol, glucose or sucrose.

10. A stable solution as claimed in claim 8 in which the polyol is present at a concentration of 20 to 500 mM.

11. A stable solution as claimed in claim 8 in which the polyol is mannitol at a concentration of 100 to 250 mM.

12. A stable solution as claimed in claim 4 in which the hybrid α-interferon is at a concentration of 0.1 to 1.5 mg/mL.

13. A stable solution as claimed in claim 5 in which the hybrid α-interferon is at a concentration of 0.1 to 1.5 mg/mL.

14. A stable solution as claimed in claim 12 in which the hybrid α-interferon is at a concentration of 0.2 to 0.4 mg/mL.

15. A stable solution as claimed in claim 13 in which the hybrid α-interferon is at a concentration of 0.2 to 0.4 mg/mL.

16. A stable solution as claimed in claim 4 which also contains a pharmaceutically acceptable polyol.

17. A stable solution as claimed in claim 5 which also contains a pharmaceutically acceptable polyol.

18. A stable solution as claimed in claim 12 which also contains a pharmaceutically acceptable polyol.

19. A stable solution as claimed in claim 13 which also contains a pharmaceutically acceptable polyol.

20. A stable solution as claimed in claim 14 which also contains a pharmaceutically acceptable polyol.

21. A stable solution as claimed in claim 15 which also contains a pharmaceutically acceptable polyol.

22. A stable solution as claimed in claim 16 in which the polyol is mannitol, glucose, or sucrose.

23. A stable solution as claimed in claim 17 in which the polyol is mannitol, glucose, or sucrose.

24. A stable solution as claimed in claim 18 in which the polyol is mannitol, glucose, or sucrose.

25. A stable solution as claimed in claim 19 in which the polyol is mannitol, glucose, or sucrose.

26. A stable solution as claimed in claim 20 in which the polyol is mannitol, glucose, or sucrose.

27. A stable solution as claimed in claim 21 in which the polyol is mannitol, glucose, or sucrose.

28. A stable solution as claimed in claim 16 in which the polyol is present at a concentration of 20 to 500 mM.

29. A stable solution as claimed in claim 17 in which the polyol is present at a concentration of 20 to 500 mM.

30. A stable solution as claimed in claim 18 in which the polyol is mannitol, glucose, or sucrose.

31. A stable solution as claimed in claim 16 in which the polyol is mannitol at a concentration of 100 to 250 mM.

32. A stable solution as claimed in claim 17 in which the polyol is mannitol at a concentration of 100 to 250 mM.

* * * * *